United States Patent [19]

Van Overloop

[11] 4,419,568
[45] Dec. 6, 1983

[54] WET DRESSINGS HEATER

[75] Inventor: Ronald R. Van Overloop, Palatine, Ill.

[73] Assignee: The Kendall Company, Boston, Mass.

[21] Appl. No.: 397,302

[22] Filed: Jul. 12, 1982

[51] Int. Cl.³ ............................................. F27D 11/00
[52] U.S. Cl. .................................... 219/441; 128/403;
  68/5 C; 219/386; 219/439; 219/401; 219/521;
  422/26; 422/307; 604/291
[58] Field of Search ............... 219/401, 386, 438, 439,
  219/440, 441, 442, 521, 524, 525, 527, 530, 211,
  212; 128/252, 403; 68/5 R, 5 C; 422/26, 300,
  307; 604/291

[56] References Cited

U.S. PATENT DOCUMENTS

| | | | |
|---|---|---|---|
| 1,979,222 | 10/1934 | Goodwin | 219/441 X |
| 2,059,911 | 11/1936 | Rebora | 219/386 X |
| 2,356,684 | 8/1944 | Miner, Jr. | 422/264 |
| 2,376,611 | 5/1945 | Miner, Jr. | 422/26 |
| 2,415,238 | 2/1947 | Emerson | 68/5 C |
| 2,443,321 | 6/1948 | Miner, Jr. | 422/300 X |
| 3,678,248 | 7/1972 | Tricault et al. | 219/439 X |
| 3,879,171 | 4/1975 | Tulis | 219/527 X |
| 3,902,044 | 8/1975 | Doyle et al. | 219/401 X |
| 4,084,080 | 4/1978 | McMahan | 219/401 |
| 4,163,896 | 8/1979 | McAvinn et al. | 219/525 |

*Primary Examiner*—Volodymyr Y. Mayewsky
*Attorney, Agent, or Firm*—Powell L. Sprunger

[57] ABSTRACT

A heater for wet dressings comprising, a case having a base with sidewalls defining a cavity, and an insert connected to the base and defining at least one recess in the cavity to receive the wet dressings. The heater has an electrical heating element in close proximity to the insert recess for heating the wet dressings, and the temperature of the heating element is controlled in the desired range of temperature of the wet dressings.

21 Claims, 4 Drawing Figures

WET DRESSINGS HEATER

BACKGROUND OF THE INVENTION

The present invention relates to heating systems, and more particularly to such systems for heating wet dressings.

Wet dressings are commonly used for therapeutic purposes, such as on abscesses and boils. The wet dressings are applied in a heated state and serve to prevent tissue encrustation, and promote blood flow and fluid drainage, with the effect of reducing swelling and its consequent pain. Such dressings are commonly packaged in specially designed foil packs which are capable of conducting and withstanding increased temperatures and internal pressures during heating. After appropriate heating, the dressings are removed from the packs, and are applied to the patient.

In the past, the dressings are commonly heated through use of radiant heating procedures. Thus, the packed dressings may be stacked below a bulb which emits infrared rays in order to heat the dressings in the foil packs. The upper pack of the stacked packs remains below the heating bulb for a set period of time, such as five minutes, after which the upper pack may be removed and the underlying packs must be sequentially heated for additional periods of time, such as three minutes each. Thus, such prior devices require an extended period of time in order to heat a series of wet dressings, and limit immediate access to a plurality of heated dressings. Moreover, the heating device does not permit storage of dressings in a heated condition, and the dressings must be applied immediately after heating in order to prevent their cooling prior to use. Further, one or more of the wet dressings may be overheated due to lack of precise control over the radiant heating procedure, resulting in possible discomfort and harm to the patient when applied to the patient's tissue. In addition, the number of dressings which may be simultaneously heated is limited by the capabilities of the heating device.

A wet dressings heating system is disclosed in U.S. Pat. No. 4,163,896, incorporated herein by reference.

SUMMARY OF THE INVENTION

A principal feature of the present invention is the provision of an improved heater for wet dressings.

The heater of the present invention comprises, a case having a base with sidewalls defining a cavity, and an insert connected to the base and defining at least one recess in the cavity to receive the wet dressings. The heater has an electrical heating element in close proximity to the insert recess for heating the wet dressings, and means for controlling the temperature of the heating element in the desired range of temperature of the wet dressings.

A feature of the present invention is that a plurality of wet dressings may be simultaneously heated in the insert recess.

Another feature of the invention is that the wet dressings may be maintained at the desired temperature range over a period of time.

Still another feature of the invention is that the heater prevents overheating of the dressings.

Thus, a feature of the present invention is that a number of dressings may be heated and stored at a precisely controlled temperature over a period of time until desired for use.

Further features will become more fully apparent in the following description of the embodiments of this invention and from the appended claims.

DESCRIPTION OF THE PREFERRED EMBODIMENTS

Figure 1:
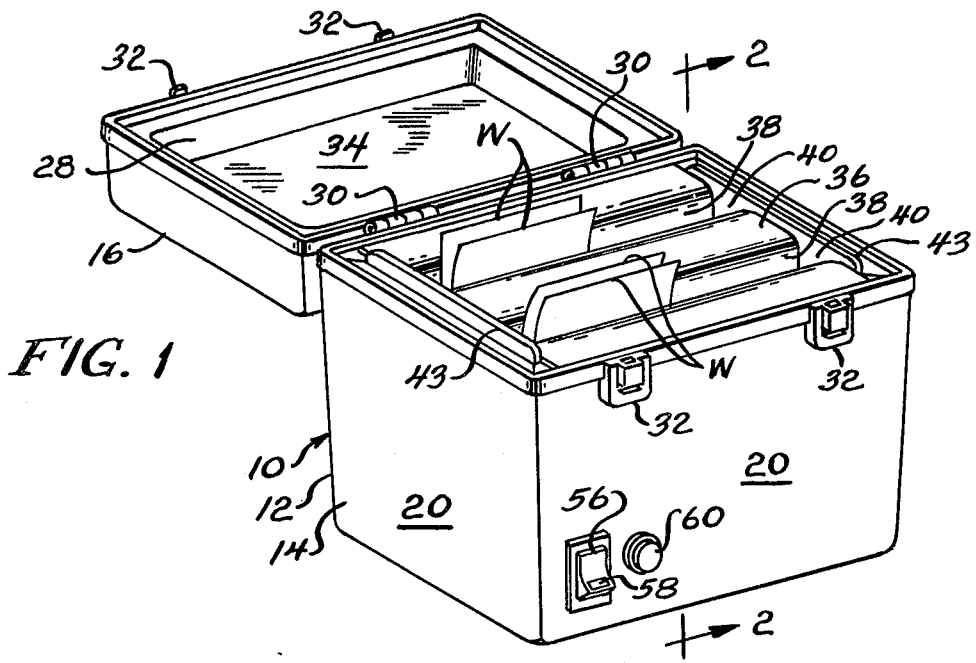
FIG. 1 is a perspective view of a heater of the present invention.
Figure 2:
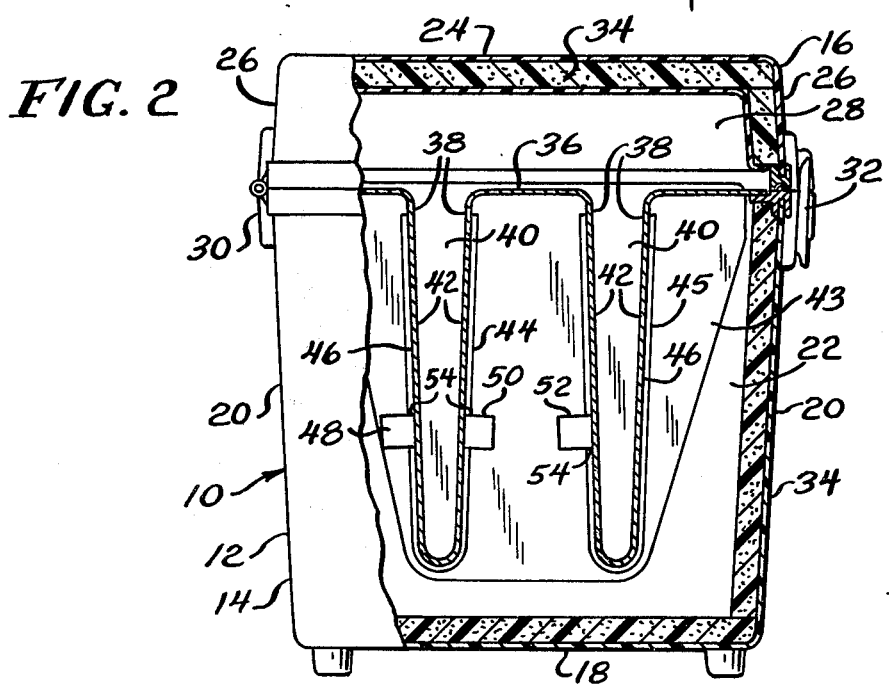
FIG. 2 is a sectional view taken substantially as indicated along the line 2—2 of FIG. 1.

Referring now to FIGS. 1 and 2, there is shown a heater generally designated 10 having a case 12 comprising a base 14 and a lid 16. The base 14 has a bottom wall 18 and a plurality of upstanding sidewalls 20 defining a cavity 22. The lid 16 has a top wall 24 and a plurality of sidewalls 26 defining a cavity 28. The case 12 has a pair of hinges 30 securing the lid 16 to the base 14, such that the lid 16 may be placed in a first closed position, as shown in FIG. 2, with the lid 16 covering the cavity 22, and a second open position, as shown in FIG. 1, with the lid 16 being removed from the base 14. The case 12 has a pair of clamps 32 to secure the lid 16 to the base 14 in the closed position of the lid 16, as shown in FIG. 2. The case 12 has a layer of insulation material 34, such as a suitable foam material, covering the bottom wall 18, sidewalls 20, top wall 24, and sidewalls 26 to minimize the escape of heat from the case 12.

The heater 10 has an insert 36, which may be constructed from a suitable metal such as stainless steel, with the insert 36 being secured to and extending across an upper portion of the base 14. The insert 36 has a pair of opposed walls 38 defining a pair of recesses 40 in the cavity 22, such that the wet dressings W may be received between the inner surfaces 42 of the opposed walls 38. The heater 10 has a pair of opposed end plates 43 to retain the insert 36.

The heater 10 has a pair of heating elements 44 and 45 secured to and substantially covering the outer surface 46 of the opposed walls 38, such that the heating elements 44 and 45 supply heat to the insert 36 and wet dressings W when current is supplied to the heating elements 44 and 45. The heating elements 44 and 45 may comprise an etched foil heater embedded in an elastic silicone rubber, such as the heating element sold by Electro-Flex Heat, Inc. of Bloomfield, Conn. The heater 10 has thermostats 48, 50, and 52 secured to the insert 36 through openings 54 in the heating elements 44 and 45. With reference to FIG. 1, the heater 10 has a double pole single throw power switch 56 with a light 58 in the switch 56 to indicate when the power to the heater 10 is on. Also, the heater 10 has a second light 60 to indicate when the heater 10 is in an initial warming condition when the light is on.

Figure 3:
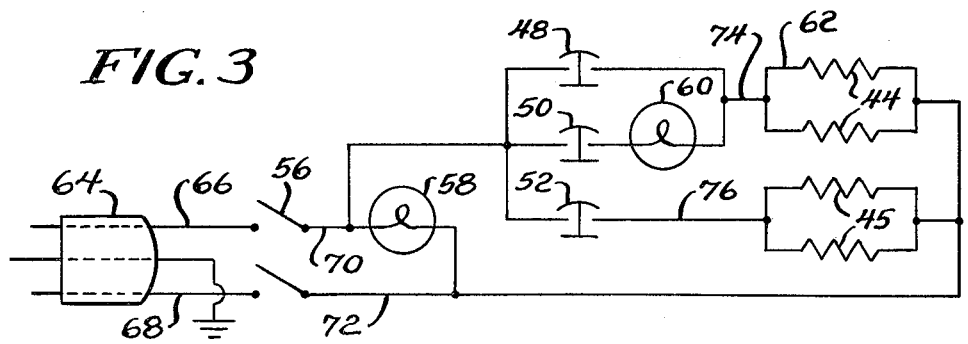
FIG. 3 is a diagrammatic view of a circuit for the heater of the present invention.

A circuit 62 for the heater 10 is illustrated in FIG. 3. As shown, the heater 10 has a plug 64 which may be secured in a wall outlet to a source of electrical power. The plug 64 is connected by a pair of leads 66 and 68 to the switch 56, such that the electrical power is disconnected from the circuit 62 when the switch 56 is open, and the electrical power is connected to the circuit 62 when the switch 56 is closed. The switch 56 is connected to a pair of leads 70 and 72, and the light 58 is connected between the leads 70 and 72, such that the light 58 is lit when the switch 56 is closed, and the light 58 is off when the switch 56 is open.

The lead 70 is connected to the thermostats 48, 50, and 52, the thermostats 48 and 50 are connected by a lead 74 to the heating element 44, and the thermostat 52 is connected by a lead 76 to the heating element 45, with the heating elements 44 and 45 being connected to the lead 72 to complete the circuit. As shown, the light 60 is in series with the thermostat 50 for a purpose which will be described below.

The desired temperature range of the wet dressings W is between 115° F. and 120° F., but when the wet dressings W are initially at room temperature a greater amount of heating is required to bring them up to the desired temperature range. The upper and lower set points of the thermostats 48 and 52 are 135° F. and 115° F., while the upper and lower set points of the thermostat 50 are 145° F. and 100° F. When the heater 10 is initially turned on by the power switch 56, the three thermostats 48, 50, and 52 are all closed, such that current is supplied to the heaters 44 and 45, and the light 60 is lit indicating that the wet dressings W are in an initial heating condition. When the thermostat 52 senses that the temperature associated with the heating element 45 is 135° F., the thermostat 52 interrupts current to the heating element 45. When the thermostat 52 subsequently senses that the temperature associated with the heating element 45 drops to 115° F., the thermostat 52 again closes and supplies current to the heating element 45. Subsequently, the thermostat 52 interrupts current to the heating element 45 when the sensed temperature is 135° F.

As previously indicated, when the power switch 56 is initially closed, both thermostats 48 and 50 are closed to supply current to the heating element 44. When the thermostat 48 senses that the temperature associated with the heating element 44 is 135° F., the thermostat 48 interrupts current to the heating element 44. However, at this time, the thermostat 50 is still closed and continues to supply current to the heating element 44 until the sensed temperature associated with the heating element 44 is 145° at which time the thermostat 50 opens and interrupts current to the heating element 44. As a result, the light 60 in series with the thermostat 50 turns off, thus indicating that the initial heating period for the wet dressings W has been completed. Next, when the thermostat 48 senses that the temperature associated with the heating element 44 is 115° F., the thermostat 48 closes and again supplies current to the heating element 44. Hence, the thermostat 50 will remain in an open configuration since the temperature associated with the heating element 44 does not drop to its lower set point of 100° F., and thus the light 60 remains in an off condition. Subsequently, the thermostat 48 again interrupts current to the heating element 44 when the sensed temperature associated with the heating element 44 is 135° F. In this manner, the thermostats 48 and 50 heat the wet dressings W a greater amount during the initial heating period in order to more rapidly obtain the desired temperature range of the wet dressings W. During operation of the heater 10 with the light 60 in an off condition, the thermostats 48 and 52 maintain the heating elements 44 and 45 at a temperature such as to maintain the wet dressings W in the desired temperature range of 115° F. to 120° F.

In use, the lid 16 is moved to the open configuration, as illustrated in FIG. 1, and a plurality of wet dressings W are inserted into the recesses 40 of the insert 36. Next, the lid 16 may be moved to the closed configuration, as shown in FIG. 2, and the clamps 32 may be closed to lock the lid 16 onto the base 14. The power switch 56 may be moved to the closed position, and the operator waits until the light 60 assumes the off condition at which time the wet dressings W are ready for use. If desired, the wet dressings W may be maintained at the desired temperature range over a period of time, and the lid 16 may be moved to the open configuration, as shown in FIG. 1, in order to remove the wet dressings W from the recesses 40 for use on a patient.

Figure 4:
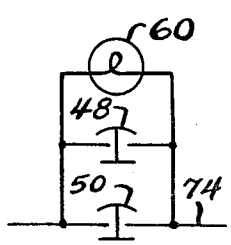
FIG. 4 is a diagrammatic view of a portion of another circuit of the invention.

With reference to FIG. 4, a portion of another embodiment of the circuit is shown. In this embodiment, the light 60 is in parallel with the thermostats 48 and 50, with the rest of the circuit shown in FIG. 3 remaining the same. When the thermostats 48 and 50 are conducting, insufficient current passes through the light 60 to energize the light. Hence, the light 60 turns off when the thermostats 48 and 50 are in a conducting state. The light 60 turns on when the thermostats 48 and 50 are not conducting to indicate that the dressings are heated and ready for use.

The foregoing detailed description is given for clearness of understanding only, and no unnecessary limitations should be understood therefrom, as modifications will be obvious to those skilled in the art.

I claim:

1. A heater for wet dressing comprising:
    a case having a base with sidewalls defining a cavity;
    an insert within the cavity of said base and defining at least one narrow recess in said insert to receive wet dressings, said recess being capable of being heated;
    an electrical heating element, electrically insulated with respect to said recess and located in close proximity to the insert recess within that portion of said cavity between the insert and the base, for heating the wet dressings;
    electrical circuit means within said cavity interconnecting said heating element and a source of electric current; and
    means for controlling the temperature of the heating element in the desired range of temperature of the wet dressings, said controlling means being a part of said electrical circuit means and comprising;
    first means for controlling current to the heating element and for sensing the temperature associated with the heating element, said first means initially supplying current to the heating element until a first temperature is sensed substantially higher than the desired temperature range of the wet dressings, said first means interrupting current to the heating element at said first sensed temperature, said first means again supplying current to the heating element at a second sensed temperature substantially below the range of desired temperature of the wet dressings, and said first means subsequently interrupting current to the heating element when said first temperature is sensed; and
    second means for controlling current to the heating element and for sensing the temperature associated with the heating element, said second means initially supplying current to the heating element until a third temperature is sensed higher than the desired temperature range of the wet dressings and lower than said first temperature, said second means interrupting current to the heating element at said third sensed temperature, said second means again supplying current to the heating element at a fourth sensed temperature below the range of desired temperature of the wet dressings and higher than said second temperature, and said second means subsequently interrupting current to the heating element when said third temperature is sensed.

2. The heater of claim 1 in which the controlling means maintains the wet dressings in a temperature range of approximately 115° F. to 120° F.

3. The heater of claim 1 wherein said case has a lid removably covering said recess.

4. The heater of claim 3 including means for releasably attaching the lid to said base.

5. The heater of claim 1 wherein said sidewalls include insulation means.

6. The heater of claim 1 wherein said insert includes a plurality of recesses to receive wet dressings, and including a plurality of heating elements associated with said recesses.

7. The heater of claim 1 wherein the insert includes a pair of opposed walls defining said recess, and in which the heating element is secured to and substantially covers surfaces of said walls opposite said recess.

8. The heater of claim 1 wherein said heating element comprises an electrical heater imbedded in an elastic material.

9. The heater of claim 1 wherein the controlling means comprises at least one thermostat.

10. The heater of claim 1 wherein said first and second means comprise first and second thermostats.

11. The heater of claim 10 wherein the set points of said first thermostat are approximately 100° F. and 145° F.

12. The heater of claim 10 wherein the set points of said second thermostat are approximately 115° F. and 135° F.

13. The heater of claim 1 including means for indicating when the wet dressings are in the desired temperature range.

14. The heater of claim 13 wherein the indicating means comprises a light.

15. The heater of claim 1 including means for indicating when said first means is supplying current to the heating element.

16. The heater of claim 15 wherein the indicating means comprises a light.

17. The heater of claim 1 including means for indicating when the first and second means interrupt current to the heating element.

18. The heater of claim 17 wherein the indicating means comprises a light.

19. A heater for wet dressings, comprising:
a case having a base with sidewalls defining a cavity,
an insert within the cavity of the base and defining at least one narrow recess in the insert to receive wet dressings, the recess capable of being heated, electrical heating element means for said recess, means electrically insulating said heating element with respect to said recess, and electrical circuit means within said case interconnecting said heating element and a source of electric current; and
means for controlling the temperature of the heating element in the desired range of temperature of the wet dressings, said controlling means being a part of said electrical circuit means and comprising:
first means for controlling current to the heating element and for sensing the temperature associated with the heating element, said first means initially supplying current to the heating element until a first temperature is sensed substantially higher than the desired temperature range of the wet dressings, said first means interrupting current to the heating element at first sensed temperature, said first means again supplying current to the heating element at a second sensed temperature substantially below the range of desired temperature of the wet dressings, and said first means subsequently interrupting current to the heating element when said first temperature is sensed; and
second means for controlling current to the heating element and for sensing the temperature associated with the heating element, said second means initially supplying current to the heating element until a third temperature is sensed higher than the desired temperature range of the wet dressings and lower than said first temperature, said second means interrupting current to the heating element at said third sensed temperature, said second means again supplying current to the heating element at a fourth sensed temperature below the range of desired temperature of the wet dressings and higher than said second temperature, and said second means subsequently interrupting current to the heating element when said third temperature is sensed.

20. The heater of claim 19 including means for indicating when the first and second means interrupt current to the heating element, said indicating means comprising a light.

21. A heater for wet dressings, comprising:
a case having a base with sidewalls defining a cavity;
an insert within the cavity of said base and defining at least a pair of generally vertically oriented parallel recesses in said insert, each said recess being in the form of a slot and having substantial width and depth dimensions and a narrow transverse dimension so as to receive a generally flat wet dressing therein, said recesses capable of being heated;
an electrical heater imbedded in an elastic material for each said recess, each heater thus being electrically insulated from its respective recess, each recess further including opposed walls having inner surfaces, defining the slot to receive a wet dressing, and outer surfaces facing said cavity, said heater being directly secured to and substantially covering said outer surfaces of the opposed walls of the recess associated therewith;
electrical circuit means within said cavity interconnecting said heating element and a source of electric current; and
means for controlling the temperature of the heating element in the desired range of temperature of the wet dressings, said controlling means being a part of said electrical circuit means.

* * * * *